US 6,660,013 B2

(12) United States Patent
Rabiner et al.

(10) Patent No.: US 6,660,013 B2
(45) Date of Patent: Dec. 9, 2003

(54) APPARATUS FOR REMOVING PLAQUE FROM BLOOD VESSELS USING ULTRASONIC ENERGY

(75) Inventors: Robert A. Rabiner, North Reading, MA (US); Brad A. Hare, Chelmsford, MA (US)

(73) Assignee: OmniSonics Medical Technologies, Inc., Wilmington, MA (US)

( * ) Notice: Subject to any disclaimer, the term of this patent is extended or adjusted under 35 U.S.C. 154(b) by 0 days.

(21) Appl. No.: 09/972,555

(22) Filed: Oct. 5, 2001

(65) Prior Publication Data

US 2003/0069590 A1 Apr. 10, 2003

Related U.S. Application Data

(63) Continuation-in-part of application No. 09/618,352, filed on Jul. 19, 2000.
(60) Provisional application No. 60/157,824, filed on Oct. 5, 1999, and provisional application No. 60/178,901, filed on Jan. 28, 2000.

(51) Int. Cl.[7] .......................... A61B 17/22; A61B 17/00; A61B 17/20
(52) U.S. Cl. ....................... 606/128; 606/114; 606/115; 604/22
(58) Field of Search ................. 606/128, 127, 606/110, 114, 115, 166, 169, 170; 604/22

(56) References Cited

U.S. PATENT DOCUMENTS

| 2,990,616 | A | 7/1961 | Balamuth et al. ........... 433/119 |
|---|---|---|---|
| 3,526,219 | A | 9/1970 | Balamuth ................... 600/565 |
| 3,565,062 | A | 2/1971 | Balumuth ................... 606/169 |
| 3,589,363 | A | 6/1971 | Banko ........................ 604/22 |
| 3,805,787 | A | 4/1974 | Banko ........................ 128/276 |
| 3,861,391 | A | 1/1975 | Antonevich et al. ........ 606/128 |
| 4,136,700 | A | 1/1979 | Broadwin et al. ........... 606/169 |
| 4,236,510 | A | 12/1980 | Hatter et al. ................ 601/2 |
| 4,474,180 | A | 10/1984 | Angulo ........................ 128/328 |
| 4,486,680 | A | 12/1984 | Bonnet et al. ........... 310/323.19 |
| 4,493,694 | A | 1/1985 | Wuchinich .................... 604/22 |

(List continued on next page.)

FOREIGN PATENT DOCUMENTS

| EP | 0293472 | 12/1988 | ........... A61B/17/22 |
|---|---|---|---|
| EP | 0541249 | 5/1993 | ........... A61F/9/007 |
| WO | WO 90/01300 | 2/1990 | ........... A61B/17/32 |
| WO | WO 95/03740 | 2/1995 | ........... A61B/17/20 |
| WO | WO 96/07377 | 3/1996 | ........... A61F/9/007 |
| WO | WO 98/35721 | 8/1998 | |
| WO | WO 98/55032 | 12/1998 | ........... A61B/17/22 |
| WO | WO 99/33404 | 7/1999 | ........... A61F/9/007 |
| WO | WO 99/35982 | 7/1999 | ........... A61B/17/32 |
| WO | WO 00/21444 | 4/2000 | ........... A61B/17/20 |

OTHER PUBLICATIONS

PCT International Search Report for International Application No. PCT/US02/31831 dated Dec. 18, 2002.

*Primary Examiner*—Eduardo C. Robert
*Assistant Examiner*—D. Austin Bonderer
(74) *Attorney, Agent, or Firm*—Palmer & Dodge, LLP; Richard B. Smith; David J. Dykeman (57) ABSTRACT

A method and apparatus for removing plaque, fatty deposits, and other occlusions from blood vessels using ultrasonic energy. The method and apparatus has particular application in removing plaque from the carotid artery in a non-thermal manner. The apparatus is designed to have as small a cross-sectional profile as possible, therefore allowing the apparatus to be used in a minimally-invasive manner. As a result, the apparatus can be used in both surgical and outpatient treatment with minimal post-operative complications and minimal damage to areas other than the area of treatment. An ultrasonic probe may include aspiration channels on its outer surface. An aspiration sheath may surround the ultrasonic probe, such that the location of an aspiration port may be varied axially relative to the ultrasonic tip.

40 Claims, 8 Drawing Sheets

U.S. PATENT DOCUMENTS

| | | | |
|---|---|---|---|
| 4,504,264 A | 3/1985 | Kelman | 604/22 |
| 4,526,571 A | 7/1985 | Wuchinich | 604/22 |
| 4,535,759 A | 8/1985 | Polk et al. | 128/24 A |
| 4,634,420 A | 1/1987 | Spinosa et al. | 604/22 |
| 4,838,853 A | 6/1989 | Parisi | 604/22 |
| 4,867,141 A | 9/1989 | Nakada et al. | 128/24 A |
| 4,870,953 A | 10/1989 | DonMicheal et al. | 128/24 A |
| 4,886,491 A | 12/1989 | Parisi et al. | 604/22 |
| 4,920,954 A | 5/1990 | Alliger et al. | 128/24 A |
| 4,922,902 A | 5/1990 | Wuchinich et al. | 604/22 |
| 4,931,047 A | 6/1990 | Broadwin et al. | 604/22 |
| 4,961,424 A | 10/1990 | Kubota et al. | 128/24 A |
| 4,962,755 A | 10/1990 | King et al. | 128/24 A |
| 4,989,583 A | 2/1991 | Hood | 128/24 A |
| 5,015,227 A | 5/1991 | Broadwin et al. | 604/22 |
| 5,026,387 A | 6/1991 | Thomas | 606/169 |
| 5,057,119 A | 10/1991 | Clark et al. | 606/169 |
| 5,057,182 A | 10/1991 | Wuchinich | 156/580.1 |
| 5,059,210 A | 10/1991 | Clark et al. | 606/169 |
| 5,062,827 A | 11/1991 | Wiksell | 604/22 |
| 5,112,300 A | 5/1992 | Ureche | 604/22 |
| 5,116,343 A | 5/1992 | Ams et al. | 606/128 |
| 5,163,421 A | 11/1992 | Bernstein et al. | 128/24.1 |
| 5,167,619 A | 12/1992 | Wuchinich | 604/22 |
| 5,171,387 A | 12/1992 | Wuchinich | 156/73.3 |
| 5,176,677 A | 1/1993 | Wuchinich | 606/46 |
| 5,180,363 A | 1/1993 | Idemoto et al. | 202/32 |
| 5,190,517 A | 3/1993 | Zieve et al. | 604/22 |
| 5,209,719 A * | 5/1993 | Baruch et al. | 604/22 |
| 5,221,282 A | 6/1993 | Wuchinich | 606/99 |
| 5,243,997 A | 9/1993 | Uflacker et al. | 128/772 |
| 5,267,954 A | 12/1993 | Nita | 604/22 |
| 5,269,297 A | 12/1993 | Weng et al. | 128/24 AA |
| 5,271,735 A | 12/1993 | Greenfeld et al. | 604/266 |
| 5,300,021 A | 4/1994 | Wuchinich | 604/22 |
| 5,304,115 A | 4/1994 | Pflueger et al. | 604/22 |
| 5,312,328 A | 5/1994 | Nita et al. | 604/22 |
| 5,312,329 A | 5/1994 | Beaty et al. | 604/22 |
| 5,324,299 A | 6/1994 | Davison et al. | 606/167 |
| 5,334,183 A | 8/1994 | Wuchinich | 606/46 |
| 5,342,292 A | 8/1994 | Nita et al. | 604/22 |
| 5,358,505 A | 10/1994 | Wuchinich | 606/99 |
| 5,366,490 A | 11/1994 | Edwards et al. | 607/99 |
| 5,368,558 A | 11/1994 | Nita | 604/22 |
| 5,380,274 A | 1/1995 | Nita | 604/22 |
| 5,382,228 A | 1/1995 | Nita et al. | 604/22 |
| 5,397,293 A | 3/1995 | Alliger et al. | 601/2 |
| 5,397,301 A | 3/1995 | Pflueger et al. | 604/22 |
| 5,405,318 A | 4/1995 | Nita | 604/22 |
| 5,417,654 A | 5/1995 | Kelman | 604/22 |
| 5,417,672 A | 5/1995 | Nita et al. | 604/533 |
| 5,427,118 A | 6/1995 | Nita et al. | 128/772 |
| 5,447,509 A | 9/1995 | Mills et al. | 606/1 |
| 5,458,612 A | 10/1995 | Chin | 606/192 |
| 5,472,441 A | 12/1995 | Edwards et al. | 606/41 |
| 5,484,398 A | 1/1996 | Stoddard | 604/22 |
| 5,498,236 A | 3/1996 | Dubrul et al. | 604/22 |
| 5,516,043 A | 5/1996 | Manna et al. | 239/102.2 |
| 5,603,445 A | 2/1997 | Hill et al. | 228/4.5 |
| 5,628,743 A | 5/1997 | Cimino | 606/1 |
| 5,630,837 A | 5/1997 | Crowley | 601/2 |
| 5,672,172 A | 9/1997 | Zupkas | 606/20 |
| 5,713,848 A | 2/1998 | Dubrul et al. | 604/22 |
| 5,720,710 A | 2/1998 | Tachibana et al. | 601/2 |
| 5,725,494 A | 3/1998 | Brisken | 604/22 |
| 5,728,062 A | 3/1998 | Brisken | 604/22 |
| 5,735,811 A | 4/1998 | Brisken | 604/22 |
| 5,741,225 A | 4/1998 | Lax et al. | 604/22 |
| 5,772,627 A | 6/1998 | Acosta et al. | 604/22 |
| 5,827,203 A | 10/1998 | Nita | 601/2 |
| 5,836,896 A | 11/1998 | Rosenschein | 601/2 |
| 5,836,897 A | 11/1998 | Sakurai et al. | 601/2 |
| 5,843,017 A | 12/1998 | Yoon | 604/22 |
| 5,846,218 A | 12/1998 | Brisken et al. | 604/22 |
| 5,891,149 A | 4/1999 | Young et al. | 606/80 |
| 5,895,370 A | 4/1999 | Edwards et al. | 604/22 |
| 5,931,805 A | 8/1999 | Brisken | 604/22 |
| 5,935,096 A | 8/1999 | Barrett | 604/22 |
| 5,935,142 A | 8/1999 | Hood | 606/169 |
| 5,935,143 A * | 8/1999 | Hood | 606/169 |
| 5,957,882 A | 9/1999 | Nita et al. | 604/22 |
| 5,964,756 A | 10/1999 | McGaffigan et al. | 606/41 |
| 5,989,208 A | 11/1999 | Nita | 604/22 |
| 5,989,209 A | 11/1999 | Barrett | 604/22 |
| 5,989,274 A | 11/1999 | Davison et al. | 606/169 |
| 6,032,078 A | 2/2000 | Rudie | 607/101 |
| 6,077,285 A | 6/2000 | Boukhny | 606/169 |
| 6,287,271 B1 * | 9/2001 | Dubrul et al. | 604/22 |
| 6,454,737 B1 * | 9/2002 | Nita et al. | 604/22 |

* cited by examiner

ABSTRACTS FOR REMOVING PLAQUE
FROM BLOOD VESSELS USING
ULTRASONIC ENERGY

APPARATUS FOR REMOVING PLAQUE FROM BLOOD VESSELS USING ULTRASONIC ENERGY

RELATED APPLICATIONS

This is a continuation-in-part of application Ser. No. 09/618,352, filed Jul. 19, 2000, which claims priority from Provisional Application Nos. 60/157,824, filed Oct. 5, 1999, and 60/178,901, filed Jan. 28, 2000, the entirety of these applications are hereby incorporated by reference.

FIELD OF THE INVENTION

The invention relates to a method and an apparatus for removing plaque, including fatty deposits and other occlusions from blood vessels. More particularly, the invention relates to a method and apparatus for ablating plaque from the carotid artery by utilizing ultrasonic energy.

BACKGROUND INFORMATION

A blockage of a blood vessel is the most frequent cause of stroke and is responsible for about 75 percent of the nearly 150,000 U.S. stroke deaths each year. Stroke ranks as the third leading killer in the United States after heart disease and cancer. There are 500,000 to 600,000 new strokes in the United States each year. As many as 3 million Americans have survived a stroke with more than 2 million of them sustaining some permanent disability. The overall cost of stroke to the nation is $30 billion a year.

A carotid endarterectomy is a surgical procedure in which a doctor removes fatty deposits from one of the two main arteries in the neck supplying blood to the brain. Carotid artery problems become more common as people age. The disease process that causes the buildup of fat and other material on the artery walls is called atherosclerosis, commonly known as "hardening of the arteries." The fatty deposits are called plaque, and the resulting narrowing of the artery is called stenosis. The degree of stenosis is usually expressed as a percentage of the normal diameter of the opening. Carotid endarterectomies are performed to prevent stroke. Two large clinical trials supported by the National Institute of Neurological Disorders and Stroke (NINDS) have identified specific individuals for whom the surgery is highly beneficial when performed by surgeons and in institutions that can match the standards set in those studies. The surgery has been found highly beneficial for persons who have already had a stroke or experienced the warning signs of a stroke and have a severe stenosis of 70 percent to 99 percent. In this group, surgery reduces the estimated 2-year risk of stroke by more than 80 percent, from greater than 1 in 4 to less than 1 in 10. In a second trial, the procedure has also been found highly beneficial for persons who are symptom-free but have a severe stenosis of 60 percent to 99 percent. In this group, the surgery reduces the estimated 5-year risk of stroke by more than one-half, from about 1 in 10 to less than 1 in 20.

A stroke occurs when brain cells die because of decreased blood flow to the brain. In some cases, small pieces of plaque in the carotid artery may break loose and block an artery in the brain. The narrowed opening in the carotid artery can be a source of blood clots that travel to the brain, can trap blood clots from other areas of the body, or can become completely clogged.

U.S. Pat. No. 4,867,141 discloses a medical treatment apparatus which utilizes ultrasonic energy for medical treatment, particularly to break up a stone formed in a living body. An endoscopic channel is used to insert a portion of the apparatus into a body cavity, where an ultrasonic transmission member is used to transmit ultrasonic vibrations to the stone which is in contact with the distal end of the apparatus. A perfusion liquid is supplied to the area of the stone as the stone is being broken up by mechanical ultrasonic vibrations. This perfusion liquid is suctioned away from the area of the stone. As a result of the suction, the perfusion liquid and broken pieces of the stone are drained away from the body cavity. The apparatus of that patent is configured with an ultrasonic transmission member which is aligned and coaxial with the central axis of the probe, and therefore is effective in treating conditions—such as stones—where the irregularity or condition to be removed is aligned with the body vessel through which the endoscope passes. The device of that patent is used on non-hydrated calcified tissue, and uses direct mechanical vibration of the calcified tissue in order to result in tissue fracture and destruction.

U.S. Pat. No. 5,176,677 discloses an endoscopic ultrasonic rotary electro-cauterizing aspirator. The background section of that patent includes some discussion of medical literature relating to prostatectomies, and in particular the Krawitt et al. technique, in which a gland can be removed using ultrasonic treatment without effecting to the prostatic capsule. However, the apparatus shown in that patent is disclosed as being useful for arthroscopic surgery. The apparatus shown in that patent includes a feature for providing irrigating fluid to the tip of the ultrasonic probe, as well as mechanisms for aspirating the area around the tip. The aspiration and irrigation features of that invention require individual passageways coaxial with the ultrasonic working tip, each connected to a source of pressurized fluid, for irrigation, or to a source of reduced pressure, for aspiration. The apparatus of that invention also includes other features adjacent the tip, such as an insulated hood for removing obstructions, and a telescopic viewing apparatus. The irrigation, aspiration, insulated hood and telescopic viewing apparatuses all increase the cross-sectional profile of the apparatus. The design of that apparatus also is such that it may only treat areas which are directly axially in front of the ultrasonic probe, and therefore which are axially aligned with the lumen or incision through which the probe is inserted.

Various other patents show apparatuses which use ultrasonic energy to fragment or transform body tissue. U.S. Pat. Nos. 5,112,300; 5,180,363; 4,989,583; 4,931,047; and 3,805,787 each show ultrasonic treatment apparatuses for use in treating various medical conditions. In each of these patents, some mechanism is shown for providing irrigation and/or aspiration in the area where the ultrasonic treatment is being performed. In each of these patents, however, the mechanisms for irrigation or aspiration are structured such that they increase the overall cross-sectional profile of the instrument. In addition, in each of those patents, the irrigation and aspiration ports are a fixed distance from one another, which may not be varied.

"Ultrasonic processing," as used in the prior art for, inter alia, orthopaedic surgery, is a technique wherein a body—either liquid or solid—is, in effect, "blasted" by ultrasonic energy. In ultrasonic processing, the ultrasonic energy produced by the ultrasonic vibrator influences water molecules found within the body tissue. The ultrasonic energy is in the form of very intense sound vibrations at a very high frequency. These intense, high-frequency sound vibrations result in powerful chemical and physical reactions in the water molecules within the body tissue. The reactions in the water molecules ultimately results in a process called "cavitation," which can be thought of as a form of cold (i.e., non-thermal) boiling of the water in the body tissue, wherein there is a rapid creation and collapse of numerous microscopic bubbles in the water.

The result of cavitation in water is a "breaking" of that fluid. The rapid vibrations in water caused by the application of ultrasonic energy to the water and the resultant cavitation can cause fatigue in the water molecules which will break bonds between the water molecules. The result is that the water changes from a liquid form into a gaseous form, i.e., converts into steam, but this conversion is done without the need for application of thermal energy to the water. The result is a "cold boiling" of the water.

When a steam bubble is created in a cold liquid, such as upon the application of ultrasonic energy to water, the steam will condense because it is surrounded by a cold liquid. As a result, a void or cavity is created. The surrounding water molecules rush in to fill that cavity; when they reach the center of the cavity, they collide with each other with great force. This process is called cavitation. Cavitation is a known phenomenon which results in shock waves running outward from the collapsed bubble. The shock waves caused by cavitation can wear away or destroy material. For example, such shock waves are known to wear away metal at the edges of an outboard motor propeller.

Ultrasonic processing or ultrasonics is the application of sound at extremely high intensity and high frequency (normally above human hearing; 20 kHz and above) so as to result in material changes. Ultrasonics are used in a number of different applications in order to change a variety of different materials. Ultrasonics accelerates both physical and chemical reactions in the materials to which ultrasonic energy is applied and these reactions, among many other things, are accomplished largely due to the action of cavitation. There are more actions inherent in bubble collapse which are of significance. As used herein, the term "bubble" refers to a space within a liquid which contains a gas or vapor. However, after that gas or vapor condenses, there is still a void or cavity in that space until an implosion occurs. Therefore the term "bubble," as used herein, also refers to the void or cavity.

One description of the manner in which cavitation is used in medical applications has been provided by Professor Lawrence Crum of the Applied Physics Laboratory at the University of Washington in Seattle, and can be found at the website:<http://nero.apl.washington.edu/harlett2/artgwww/acoustic/medical/medical.html>. Professor Crum, writing about lithotriptry—in which a kidney stone is broken with ultrasonic energy—has stated that "[w]hen pressure surrounding a bubble falls below the vapor pressure of the liquid, the bubble fills with vapor and grows explosively. The bubble collapses violently when pressure returns. If the collapse occurs near a boundary, such as [a] targeted kidney stone, a high velocity liquid jet is formed that impacts the boundary with great force. These extremely violent processes are thought to play a major role in stone destruction and associated tissue damage."

In addition to erosion or ablation of surfaces by the jet, cavitation causes many other actions. Notable among these in a purely physical sense is the action of intense shock fronts generated by imploding cavitation bubbles against kidney stones (lithotriptry), gall stones, tumors, and other intrusions in the body. Some of this action can also be accomplished by direct impact of a vibrating ultrasonic tool tip, but no (or minimal) cavitation is involved.

SUMMARY OF THE INVENTION

It is an object of the invention to provide a method and an apparatus for removing plaque, fatty deposits and other occlusions from the inner lining of blood vessels, particularly the carotid artery, using ultrasonic energy.

It is another object of the invention to provide an ultrasonic medical device capable of destroying and emulsifying plaque, fatty deposits and other occlusions, which can develop along the wall of the carotid artery, through cavitation with a high efficiency by means of a flexible probe operating in a transverse mode. As used herein, a transverse mode of operation is used to describe a flexible probe with a plurality of nodes and anti-nodes along the length of the probe.

It is a further object of the invention to provide a method and apparatus for removing plaque buildup from arterial walls which does not require direct contact with the wall and thereby avoids any potential damage to the artery.

The apparatus of the present invention is designed to have a small cross-sectional profile, therefore allowing the apparatus to be used in a minimally-invasive manner, either through the use and application of a small surgical cut down procedure to expose the artery or through the insertion of a small vascular introducer and the subsequent insertion of an ultrasonic probe to apply the energy source. In particular, the device according to the present invention may operate to remove deposits in the carotid artery from the internal lumen of the vessel outwards without necessarily requiring touching or direct abrasion of the vessel walls of the artery, which might otherwise be necessary with conventional methods and which can lead to damage of the artery walls. The application of the ultrasonic energy is applied in the lumen, wherein the energy migrates from the probe outward towards the obstruction or luminal constriction. Thus the microfragmentation of the materials occurs in a controlled fashion. On the other hand, traditional means of Carotid surgery typically requires the peeling of the occlusive materials from that of the vessel wall. This maximum contact fashion—where the plaque is "torn" from the vessel—causes secondary damage to the vessel. The present invention is advantageous in that it can be used in both traditional surgical sites and out-patient treatment with minimal post-operative complications and minimal damage to areas other than the area of treatment. The present invention therefore provides distinct advantages over the prior art in the treatment, and therefore provides an improved method of removing plaque from the carotid artery. It is to be understood, however, that although the present invention is designed for removing plaque from the carotid artery, its small cross-sectional profile makes it useful for treatment of any condition wherein minimally invasive techniques are advantageous and reduce post-surgical complications, and the present invention is therefore not limited to the treatment of removing plaque from the carotid artery. For example, the removal of plaque, fatty deposits and other occlusions in other blood vessels is possible using the invention.

The probe of the present invention is specifically designed to have a minimal cross-section, particularly for use for removing plaque from the carotid artery, thereby minimizing post-procedure complications and discomfort to the patient because larger sizes are more difficult to insert and uncomfortable. One way in which the present invention allows the cross-sectional profile of the probe to be minimized is by allowing aspiration to occur through grooves or channels on the outer surface of the probe. In this way, there is no need for an additional tubular aspiration sheath to be inserted into the carotid artery, to thereby provide a aspirating path.

The device is capable of reducing materials to levels equal to or smaller than 10 microns. With regard to remaining in the blood stream, it is known that particulate material of this size does not pose any health concerns. There are several ways to accomplish aspiration. For instance, a series of grooves or channels on the probe may be used. Instead, a standard vascular introducer can be used whereby aspiration is caused by the placement of an aspiration source on the luer lock fitting of the vascular introducer. In another embodiment, hollow tubes (as in a central lumen or an outer sheath that sits around the probe) can be used to draw and remove destroyed materials from the surgical site. This can be accomplished with a suction source at the handle or via the use of an induced aspiration through the ultrasonic motion of the probe or negative wave to pull the particulate back and out of the probe and surgical site. In each of these methods a relatively small amount of irrigation, e.g., approximately 10 ml per minute, may be provided to act as a lubricant to the site.

The terminus or termini of the irrigation passage can be located at the tip of the probe. Alternatively, the terminus or termini can be lateral to the probe tip—determined by the frequency of the system and the location of the nodes and anti nodes.

An object of the present invention is to provide a device and method for removing plaque from a vessel that is non-thermal. This is accomplished by the application of transverse ultrasonic energy which is extremely efficient, requiring substantially less energy to be delivered to the probe to stimulate cavitation. As a result of the reduced energy required, less actual losses in energy are realized during operation. Accordingly, because of the use of cavitation as the mechanism for destroying and emulsifying plaque, together with the use of irrigation and aspiration, the method and apparatus of the present invention can destroy and remove plaque within a range of temperatures of ±3° C. from normal body temperature. Studies now show that this temperature range can be reduced even further. Therefore, complications attendant with the use of thermal destruction or necrosis of tissue—such as swelling or edema—as well as loss of elasticity are avoided.

Various means to remove plaque from blood vessels are known in the art. For instance, carotid surgery can be accomplished by making an incision through a patient's skin to expose the vessel, cross clamping the vessel to preclude flow, making an incision to open the vessel itself, removal of the occlusion, and closure of the vessel and the skin. Additionally, in a similar procedure, a bypass line can be used to allow for the small flow of blood to the brain during the procedure prior to the cross clamping and cessation of flow.

It is an object of the invention to provide a means to remove plaque from blood vessels without precluding blood flow. This is accomplished by avoiding contact with the arterial wall by inserting the probe into the vessel—like that of a standard vascular introducer stick. The probe sits in the vessel—in the middle of the lumen—surrounded by the occlusive materials.

The probe of the present invention, because of its significantly reduced cross-sectional profile, can be made to be flexible or bendable. The probe can be of a cross-section sufficiently small that the material of the probe is bendable through a wide range of articulation angles. The probe may be housed in an articulated catheter or sheath, which catheter or sheath can be fabricated to be bendable or articulated. As a result, the present invention can be adapted to allow for the probe to activate and treat even areas of the body which are not axially aligned with the channel or lumen through which the probe is inserted. The articulation of the probe of the present invention allows for a "windshield wiper" action of the probe tip, thereby creating a cone or arc sweep, greatly increasing the area of effect of the treatment through an incision.

The probe of the present invention is particularly useful in a treatment technique in which the treated area may be imaged by ultrasound imaging, in particular color ultrasound. The vibrating length of the probe echogenically produces a pronounced and bright image on ultrasound, and therefore is readily viewable by the surgeon or physician, greatly increasing the ease of use and effectiveness of treatment.

The probe of the present invention is particularly amenable, because of its small size, to the use of a flexible fiberoptic viewing device. The device preferably includes a fiberoptic cable tip which is fed with the probe—either attached to the probe or separate from the probe—and which cable is connected to a fiberoptic viewing eyepiece which is not connected to the handle or other equipment of the ultrasonic mechanism. In this way, manipulation of the viewing system is reduced to a minimum. The fiberoptic cable preferably includes a central optical viewing cable surrounded by illumination fibers. The fiberoptic cable may be located inside of a flexible sheath portion of the device, located on top of the flexible sheath, or may be located on top of a rigid sheath of the device.

The method of the present invention, because it uses ultrasonic energy prevents damage to the surrounding artery during insertion, treatment and removal, and also reduces or eliminates tissue damage, irritation and swelling in the patient.

The present invention also provides advantages to the physician rendering the treatment. The present invention is safer for the physician, because the components of the apparatus and method of the present invention deliver only ultrasonic energy, and as a result the ultrasonic energy's affect is based on tissue planes and their hydration levels. Furthermore, the area in which the cavitation is effective in the apparatus of the present invention is an area on the order of 1–2 mm around the ultrasonic probe. As a result, the present invention allows a much higher degree of control of the affected area than prior art techniques. The present invention results in the destruction of no carotid artery wall tissue.

Another advantage of the present invention relates to the size of the particulate material broken down from the plaque. In all other applications used to remove occlusive materials, the operator is required to be vigilant in removing large particulate within the blood stream. This is because particulate larger than 500 microns may have significance to the patients overall health. However, in the present method, the application of ultrasonic energy towards the controlled destruction and removal of plaque results in particulate on the order of 10 microns or less. Thus, unlike with previously known methods, there does not appear to be a need for the down stream filters.

Traditional methods for removal of materials and exudate is through the use an aspiration mechanism which provides suction through a suction passage which is part of the probe. These traditional methods use irrigation fluid flow that is injected into the site where the procedure is being conducted, in conjunction with aspiration to remove the tissue from the surgical site. As discussed above, however, providing both irrigation and aspiration to the surgical site has, in prior art apparatuses, resulted in a probe of relatively large cross-sectional profile, and therefore that the treatment apparatus be substantially larger than the ultrasonic probe needed for conducting the procedure. These prior art apparatuses used concentric tubes wherein the irrigant is normally provide through a central core of the probe and the aspirant is provided an outer concentric tube and lumen.

Prior art apparatuses also maintain a strict orientation of the suction and the irrigation mechanism, such that the inner and outer lumens for irrigation and aspiration remain in a fixed position relative to one another, generally in a position closely adjacent the area of treatment. Additionally, if the probe is turned into an aspiration system, a problem arises in that the only location for fluid flow is at the tip of the probe, As a result, all the pressure (suction force) is focused there at this point within the vascular tree. Because of the tortuous nature of the vessels, single point suction tends to either clog or cause minor damage to the vessel.

One of the means of irrigation and aspiration in the present invention is to drill small holes or fenestrations along the length of the probe. Such fenestration are strategically placed at specific points of minimal stress due to the transverse cavitation. The use of fenestrations provides additional benefits. For example, in irrigation mode there is less of a focal pressure point out of which fluid is blown. Instead, fenestratrations allow for relatively diffuse irrigation along and around a length of the probe. Similarly, as for aspiration, by allowing suction to occur along the length of the probe, the suction pattern is greater. Among other possible benefits, this helps to prevent damage to the vessel wall and results in relatively more complete aspiration because of the larger suction pattern.

Thus, the irrigation lumen does not extend beyond the suction lumen (i.e., there is no movement of the lumens relative to one another) and the suction is designed to pick up any fluid and/or tissue remnants within the defined distance between the two lumens. The present invention, which uses grooves or channels on the outside of the probe for aspiration, or very small diameter hollow probes (~30 micron ID) allows for the distance between the irrigation and aspiration lumens to be varied, thereby allowing a reduced cross-sectional profile of the instrument inserted in to the patient's body. In the present invention, an axially movable aspirating catheter or sheath may move along the length of the probe, to thereby vary the position of the aspiration lumen relative to the probe tip and the irrigation lumen or lumens. Central aspiration within hollow probes— especially those that are ~0.020 in. diameter or smaller— allows for a flexible probe as well. This allows for the aspiration lumen, and the associated aspiration structure— except for the grooves or channels on the probe—to be located outside the patient's body.

In the application of the ultrasonic energy of the present invention the probe diameter is substantially smaller than that of traditional ultrasonic probes, and therefore is ideally designed for minimally invasive procedures. The present invention therefore relates to the application of small diameter probes, which can be inserted into a small diameter body vessel to thereafter use a cavitational effect to remove plaque. In order to increase the area of treatment which is effective in the small probe of the present invention, the irrigation lumens can be transverse to the axis of the probe, i.e., can open on the sides of the probe body. In this way, the maximum area of the probe tip is used to provide ultrasonic treatment and cavitational energy.

The probes used with the present invention are shaped to allow easy insertion, and so that they are not sharp so as to present the risk of tissue damage during insertion. The probes preferably include a taper that accommodates the insertion of the probe into the tissue through the application of the ultrasonic energy, wherein the energy is amplified through the transition from a larger mass to a smaller mass. The tapered shape of the probe, usually that of a cone, sphere, or hemisphere, ovoid tear drop shape is particularly useful in surgical applications as the tissue rent or tear caused by the insertion of the probe into the vessel is usually caused via a mechanical action of a needle or other sharp object, and not usually as a result of ultrasonic drilling of the probe. Irrespective, as the energy deposited by the probe is very low, and the round shape of the probe tip is formed, there is no additional energy departed upon the vessel to cause it to tear or that would otherwise cause a tear to expand beyond that of the initial penetration point.

Similarly, the tapered shape of the probe minimizes the overall size of the penetration point through the tissue, as the ultrasonic energy is focused at the extreme length of the flexible portion of the probe. The energy emanates for a defined length along this portion of the probe, and diminishes in transverse amplitude once specific transition barriers and shapes have been induced into the design.

In accordance with a preferred embodiment of the invention, an ultrasonic medical device comprises an ultrasonic vibration generator that generates vibration along its longitudinal axis. The ultrasonic vibration is transmitted through an ultrasonic coupler and a series of transformer sections that amplify the ultrasonic vibration. A flexible member is coupled to the distal end of the transformer sections, and is thus supplied with a longitudinal vibration at its base by the transformer sections. The flexible member is designed so that it converts the longitudinal vibration into a standing wave that runs along the length of the flexible member. The standing wave produces a series of nodes and anti-nodes along the length of the flexible member. Each of the anti-nodes produces cavitation in fluids in contact with the probe. The cavitation of the fluids causes destruction of adjacent plaque. Thus, in this manner, the entire length of the flexible member becomes a working surface that may be utilized for destroying plaque.

The invention, therefore, includes a number of advantageous features which make it particularly useful for minimally-invasive procedures. First, it allows for the application of ultrasonic energy to plaque, such as that which lines the carotid artery, via a small diameter probe that is able to traverse a vessel or opening, and which can remove plaque through the action of cavitation on the plaque. Second, the invention has the ability to make a small penetration into and through a body vessel, or to create a small penetration in the body, and thereafter allows the probe to be directed to the blood vessel to be treated, such as the carotid artery. Third, the invention allows, through the action of cavitation and a movement by the surgeon of the ultrasonic tip throughout the treated area, the creation of a large cavity, so that the cavity is larger than the size of the probe. Fourth, the apparatus of the invention may be designed with a stiffened outer member, within which a softer malleable or bendable member resides, which therefore allows the ability to insert a probe into the body, without extreme torsion and bending on the anatomy. This malleability also allows the probe to be bent or articulated so that it can reach areas which are not axially aligned with the lumen or passage into which the probe is inserted. Fifth, the invention allows the ability to remove debris at the point of the procedure. Sixth, the present invention allows the ability to irrigate the cavitation site via the ultrasonic probe—both when the probe is rigid and when the probe is flexible and malleable. Seventh, the present invention allows the use of ultrasonic energy which is applied to plaque and fatty deposits selectivity, because it uses energy in a frequency range—20 kHz to 80 kHz—such that it imparts the energy specifically to hydrated (water-laden) plaque and fatty deposits. As a result, there is little or no energy imparted to the arterial wall itself. This selectivity in the application of energy therefore avoids damage to the artery. Eighth, the present invention allows the use of bending, flexing or articulated probe, which limits the amount of force placed upon the probe as it is advanced forwards. In this way, the force applied on the probe is decreased through the bend, i.e., less pressure is imparted on the tip of the probe, thereby decreasing the potential for accidental penetration of tissue by the probe through pure physical force. That disadvantageous result might have occurred in a similar application of force using a straight probe into the prostatic capsule.

An important feature of the present invention is that it is non-thermal. The use of a procedure in which heat or thermal energy is not used is important, and the present invention produces very low heat, and the excursion of heat is limited to the immediate area associated with the acoustic wave that is ablating the plaque. The present invention, through the use of ultrasonic energy together with irrigation and aspiration, can produce treatment within a range of normal body temperature in the treated area of ±3° C. Furthermore, collateral irrigation causes the residual tissue to remain within a narrow range around normal physiologic temperatures throughout the procedure of the present invention. Due to the lack of heat in the present invention, and the immediacy of the plaque removal process, the residual tissue exhibits remarkably little to no inflammatory response, thereby producing little fibro intimal hyperplasia edema (swelling) of the vessel. As such, loss of vessel patency or vessel internal diameter is avoided.

The ultrasonic tip of the present invention, because it uses cavitation as the mode of plaque removal, does not have to be sharp. Rather, soft flexible shapes are preferred because penetration is caused by a mechanical penetration of the vessel not cavitation, and not by the physical shape of the probe. Therefore, the tip can be smooth and small, making insertion less traumatic and less prone to residual tissue damage.

In the present invention, the location of the probe can be determined via the use of a medical visual ultrasound device. Once the probe is located, the bending or flexure of the probe tip can be monitored. This enhances the physician's ability to see and direct the ultrasonic probe during treatment, and is the result of the high frequency vibrations at the tip.

The ultrasonic energy to be applied to a particular treatment site is a function of the amplitude and frequency. In general, the throw rate or amplitude of the energy supplied by the apparatus of the present invention is in the range of 150 microns to 350 microns, and the frequency in the range of 20–80 kHz. Larger probes will use the lower frequencies while smaller probes will use the higher frequencies.

DETAILED DESCRIPTION

Figure 1:
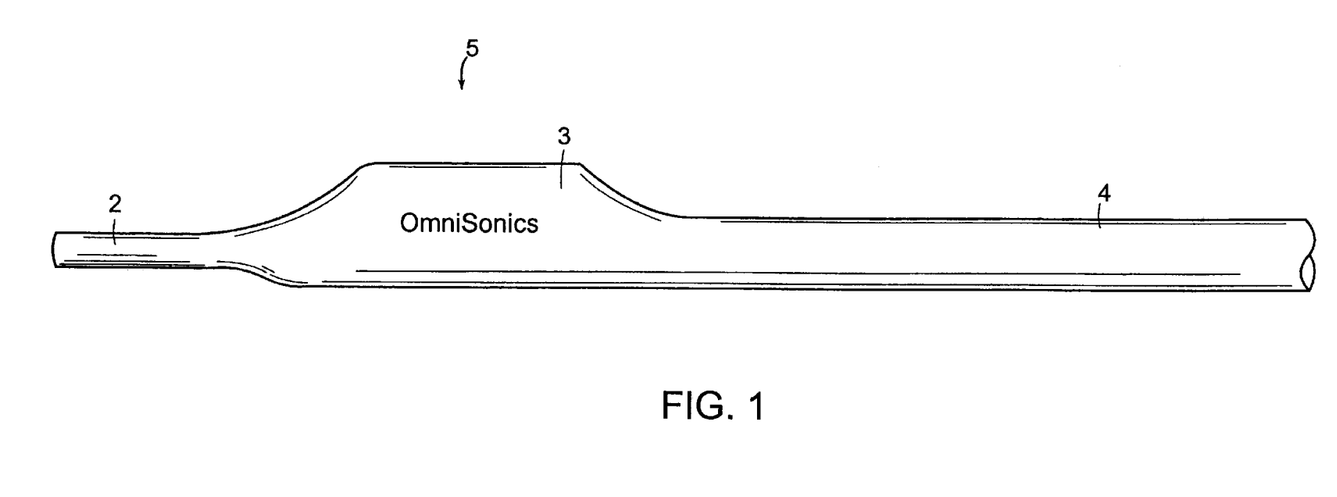
FIG. 1 is a side elevation view of handle of the ultrasonic treatment apparatus of the present invention.

FIG. 1 shows an embodiment of a handle 5 used with the present invention. The handle 5 is composed of an irrigation fitting or luer 2, a grasping area 3, and a probe fitting 4. The irrigation fitting or luer 2 is configured for connection with a flexible tube which is in turn connected to a source of pressurized irrigating fluid, such as water. The grasping area 3 is shaped for grasping by the hand of the apparatus operator, such as a surgeon, and may include one or more trigger or button mechanisms for activating and deactivating various features of the apparatus, such as suction, irrigation, power, etc.

Figure 2:
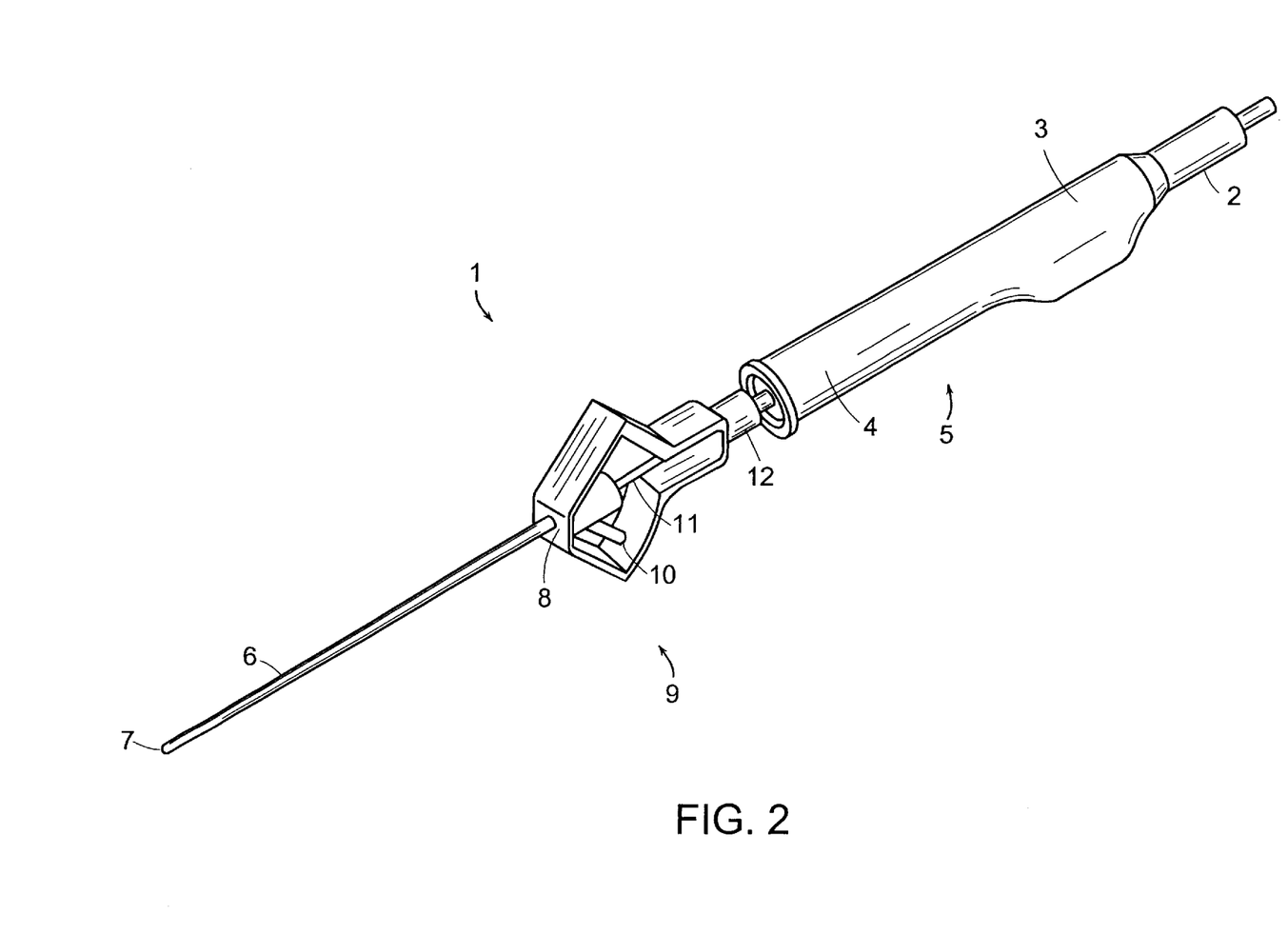
FIG. 2 is a perspective view of a first embodiment of the ultrasonic treatment apparatus of the present invention.
Figure 3:
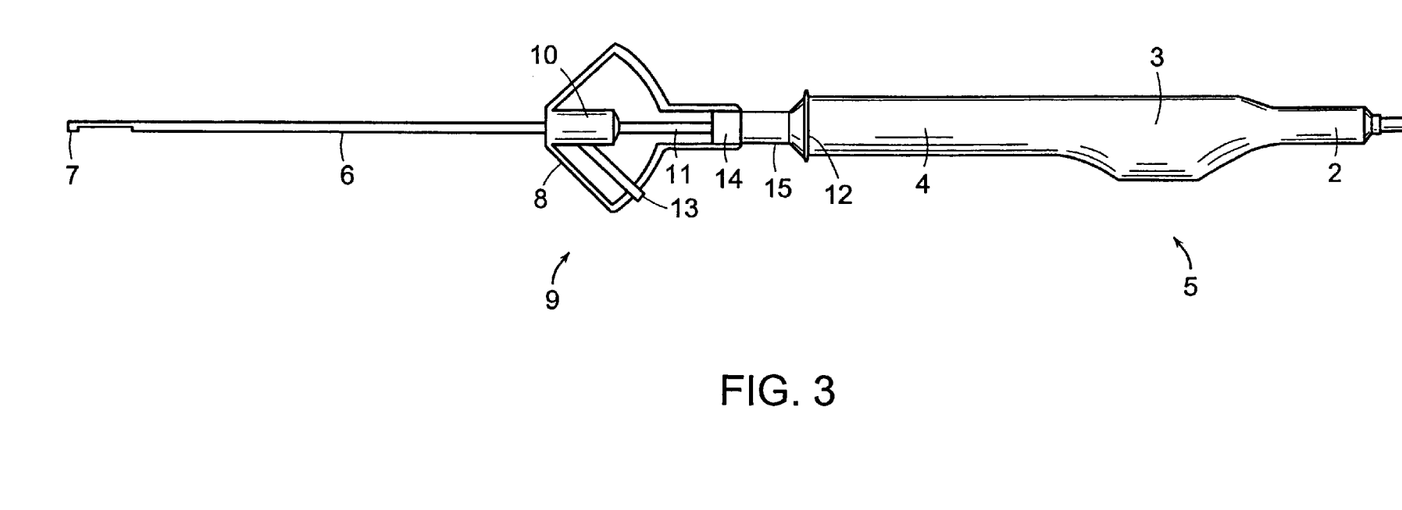
FIG. 3 is a side elevation view of the embodiment of FIG. 2.

FIGS. 2 and 3 show an embodiment of the ultrasonic treatment apparatus 1 of the present invention, which includes the handle 5 shown in FIG. 1. The ultrasonic treatment apparatus 1 includes an ultrasonic probe 6 with an ultrasonic probe tip 7. The ultrasonic probe 6 is axially movably mounted within an aspiration sheath or catheter 70, so that the probe tip 7 may move axially inwardly and outwardly relative to the distal end of the aspiration sheath or catheter 70. The ultrasonic probe 6 and aspiration sheath or catheter 70 are both mounted in an aspiration shroud 9, which includes an aspiration shroud housing 8. Within aspiration shroud housing 8 is an aspiration end 10 of aspiration sheath or catheter 70, which transmits suction or negative pressure to the interior of aspiration sheath or catheter 70. The aspiration end surrounds, and is sealed against, the ultrasonic transmission element 11 which extends to, and forms a proximal portion of, the ultrasonic probe 6. The aspiration end 10 is connected an aspiration fitting or luer 13. The aspiration fitting or luer 13 is configured for connection with a flexible tube which is in turn connected to a source of reduced pressure. The aspiration sheath is slidable relative to handle 5 and probe 6, thereby allowing the distance between the ultrasonic tip 7 and the distal end of the aspiration sheath or catheter 70 to be varied. An actuation mechanism 12 may extend from the aspiration shroud 9 to the handle 5, and is surrounded by suitable covers 14 and 15.

Figure 4:
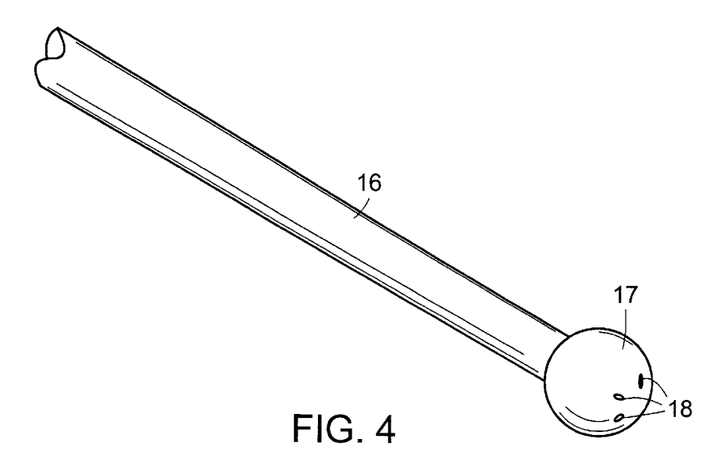
FIG. 4 is a perspective view of one embodiment of an ultrasonic tip of the present invention.

FIG. 4 shows an embodiment of an ultrasonic probe 16 and ultrasonic probe tip 17 of the present invention. The body of the ultrasonic probe 16 in the embodiment of FIG. 4 is preferably slightly tapered from the distal end to the proximal end. The ultrasonic tip 17 is in the form of a ball-shaped projection from the end of the ultrasonic probe 16. This shape of the ultrasonic tip 17 eliminates any sharp edges or surfaces on the tip which could result in damage to tissue during insertion, treatment or removal. Similarly, although not shown in the FIGS., ultrasonic tip 17 may take on a variety of other shapes. For instance, the tip can be bent into a d-shape. As tip 17 is constructed from a flexible wire—which can be bent and shaped without affect to the energy that is distributed to the probe—tip 17 can be configured such that it conforms to a pre-defined shape once within the lumen.

The ultrasonic tip 17, at its distal surface, includes one or more irrigation ports 18. The irrigation ports 18 are all connected to an internal irrigation passage, preferably centrally located in the ultrasonic tip 17 and the ultrasonic probe 16. Although not shown in FIG. 4, the ultrasonic probe 16 could have, extending along its length, one or more grooves or channels for aspiration, as discussed in more detail below.

Figure 5:
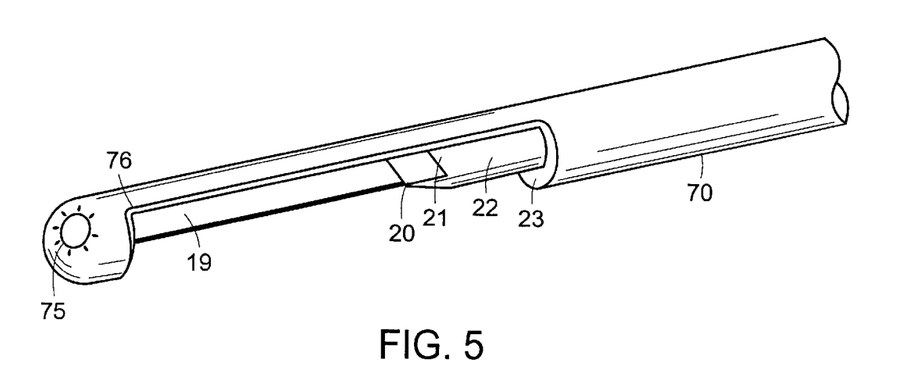
FIG. 5 is a perspective view of a second embodiment of an ultrasonic tip of the present invention.

FIG. 5 shows a second embodiment of the ultrasonic probe aspiration sheath or catheter of the present invention. The embodiment of FIG. 5 is particularly useful for treating conditions wherein the treatment area dangles or is loose; in particular, the embodiment of FIG. 5 is useful in gynecological treatments. In the embodiment of FIG. 5, the tip 75 of the aspiration sheath or catheter 70 is a rounded end. The aspiration sheath or catheter 70 includes a lateral slot or opening 19 on one side. The ultrasonic probe 23, with an ultrasonic tip 21 which may include a bevel 20 is mounted for axial sliding movement within the aspiration sheath or catheter 70. At least one aspiration passage 23 is created in the space between the ultrasonic probe 22 and the interior wall of the aspiration sheath or catheter 70. Accordingly, as suction is applied to the aspiration fitting or luer 13, a negative pressure or suction is formed at the aspiration passage 23, to draw away any destroyed or cavitated plaque and any residual or irrigation fluid.

At the proximal end of the tip 75 is a grasping surface or backstop 76. This grasping surface or backstop 76 serves as an opposed surface to the ultrasonic tip 21, thereby allowing dangle or loose treatment areas to be grasped during treatment. In operation, the aspiration sheath or catheter 70 is directed to a treatment area, until the dangling or loose treatment area falls into the lateral slot or opening 19. During this step, the ultrasonic probe 23 is in a retracted position, as shown in FIG. 5. Thereafter, the ultrasonic probe 23 is advanced axially outward, until the dangling or loose treatment area is clamped between the ultrasonic tip 21 and the grasping surface or backstop 76. Thereafter, the ultrasonic vibration generator is activated, such that ultrasonic energy is transmitted to the ultrasonic tip 21. As a result, the grasped treatment area is treated using ultrasonic energy and the resulting cavitation.

Figure 7:
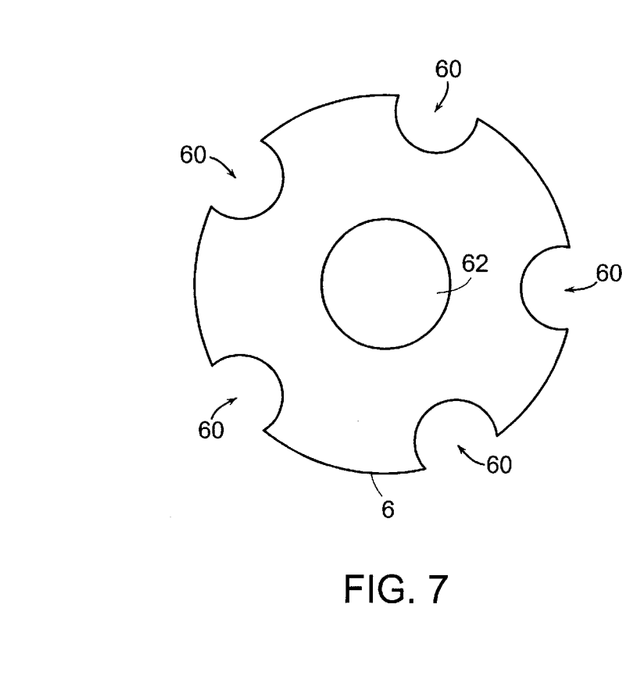
FIG. 7 is a radial cross-sectional view through an embodiment of an ultrasonic probe of the present invention.
Figure 9:
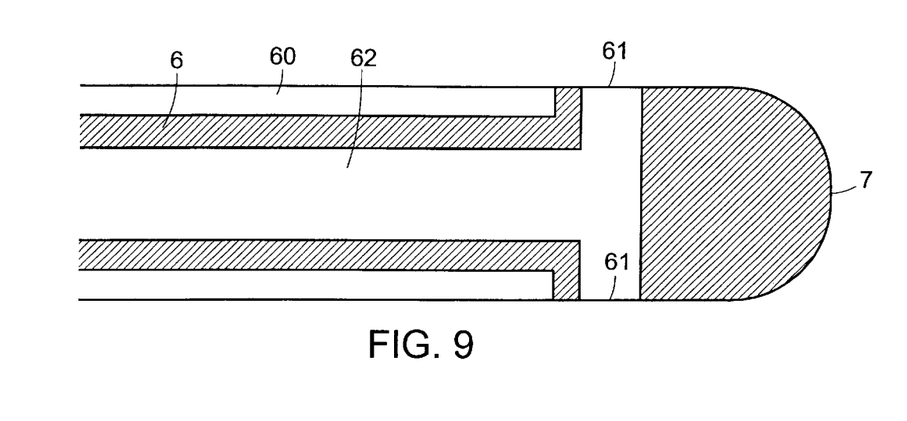
FIG. 9 is an axial cross-section of one embodiment of an ultrasonic treatment probe of the present invention.

FIGS. 7 and 9 show a radial cross-section through an ultrasonic probe 6 according to one embodiment of the invention. The probe 6 includes a central passage 62 which is connected to the irrigation fitting or luer 2. The central passage 62 terminates in two lateral lumens 61, located on the sides of the probe 6. The central passage 62 is used to transmit an irrigating fluid to the area around the ultrasonic tip 7, to thereby regulate the temperature of the treatment site. The irrigation fluid, together with the cavitational action of the ultrasonic tip 7, allows the treatment site to be regulated to a temperature of ±3° C. of normal body temperature. Furthermore, because the lumens 61 do not pass through the ultrasonic tip 7, the effective area of treatment of the ultrasonic tip 7 is increased.

As shown in FIGS. 7 and 9, the outer surface of the ultrasonic probe 6 includes one or more grooves or channels 60. These grooves or channels, although straight in FIG. 8, could spiral along the length of the ultrasonic probe 6. The grooves or channels 60 are used to aspirate fluid and tissue fragments from the treatment site, as the result of negative pressure or suction applied at the proximal ends of the grooves or channels 60. As a result, fluid and tissue fragments travel down the grooves or channels 60 and away from the treatment site, thereby preventing fluid and fragments from interfering with the ultrasonic processing and cavitation of additional tissue.

Figure 6:
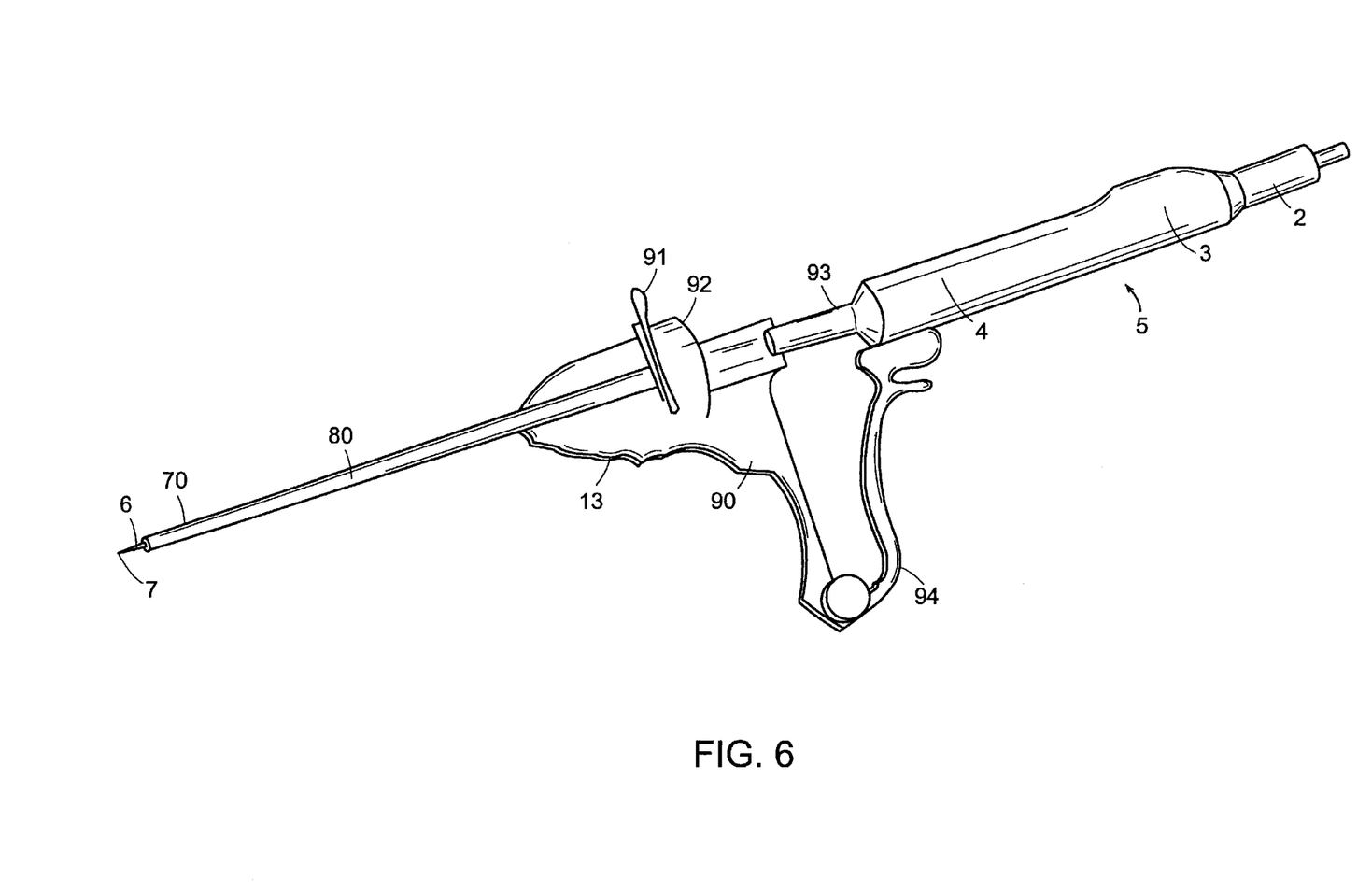
FIG. 6 is a side elevation view of a second embodiment of an ultrasonic treatment apparatus of the present invention.
Figure 8:
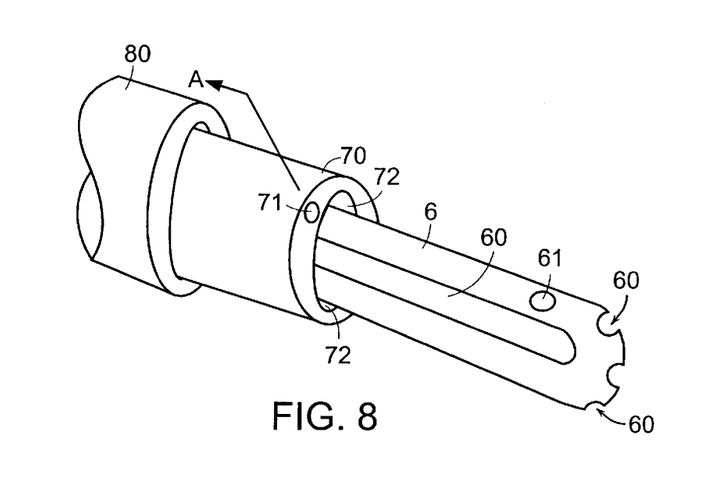
FIG. 8 is an axial cross-section of one embodiment of an ultrasonic treatment probe of the present invention.

FIGS. 6 and 8 show features of an ultrasonic treatment apparatus of another embodiment of the present invention. As shown in FIG. 6, the ultrasonic treatment apparatus has an ultrasonic probe 6 with an ultrasonic tip 7. The ultrasonic probe 6 is housed in, for slidable movement within, a flexible articulation sheath 70. The flexible articulation sheath 70 is, in turn, housed in, for slidable movement within, a rigid sheath 80. Rigid sheath 80 is connected to, for movement with, a retracting housing 90. The retracting housing 90 is connected to a retracting trigger 94, which is pivoted on the handle 5. The retracting housing 90 may include an aspiration fitting or luer 13, which is configured for connection with a flexible tube which is in turn connected to a source of reduced pressure. As discussed in more detail below, the aspiration fitting or luer 13 is connected to the interior of the flexible articulation sheath 70.

An articulation trigger 91 may be housed on the retracting housing 90. Articulation trigger 91 is connected to an articulation wire 71 discussed in more detail below. A trigger 92 may also be housed on the retracting housing 90. A cover 93 may cover components between the retracting housing 90 and the handle 5.

FIG. 8 shows the details of the proximal end of the ultrasonic apparatus of FIG. 6. The ultrasonic probe 6 may include one or more grooves or channels 60 which are used to provide aspiration to the area around the ultrasonic tip 7. One or more irrigation lumens 61 may provide irrigating fluid to the area around the ultrasonic tip 7. The ultrasonic probe 6, which, because of its small cross-sectional profile and the material of which it is constructed, is somewhat flexible so that it may be bent or articulated. The ultrasonic probe 6 fits within, for axial movement, the articulation sheath 70, which is made of a relatively flexible and resilient material. The space 72 between the ultrasonic probe 6 and the articulation sheath 70, together with the grooves or channels 60, form aspiration passages. The articulation sheath 70 may include, at one or more locations around the circumference of the articulation shaft 70, one or more embedded articulation wires 71, with a distal end affixed to the articulation sheath 70. The proximal end of the articulation wire 71 is affixed to the articulation trigger 91. The articulation sheath 70 is housed within, for axial movement, the rigid sheath 80. Rigid sheath 80 is made of a relatively rigid material.

When the rigid sheath 80 is slid back away from the distal end of the articulation sheath 70, and the articulation wire 71 is pulled axially inwardly by the articulation trigger 91, the articulation sheath will bend or articulate in a bending or articulation direction A. As a result, the ultrasonic probe 6 and ultrasonic tip 7 will bend or articulate in articulation direction A. In this way, the ultrasonic can be used to reach locations which are not axially aligned with the lumen or vessel through which the ultrasonic probe 6 is inserted.

Figure 10:
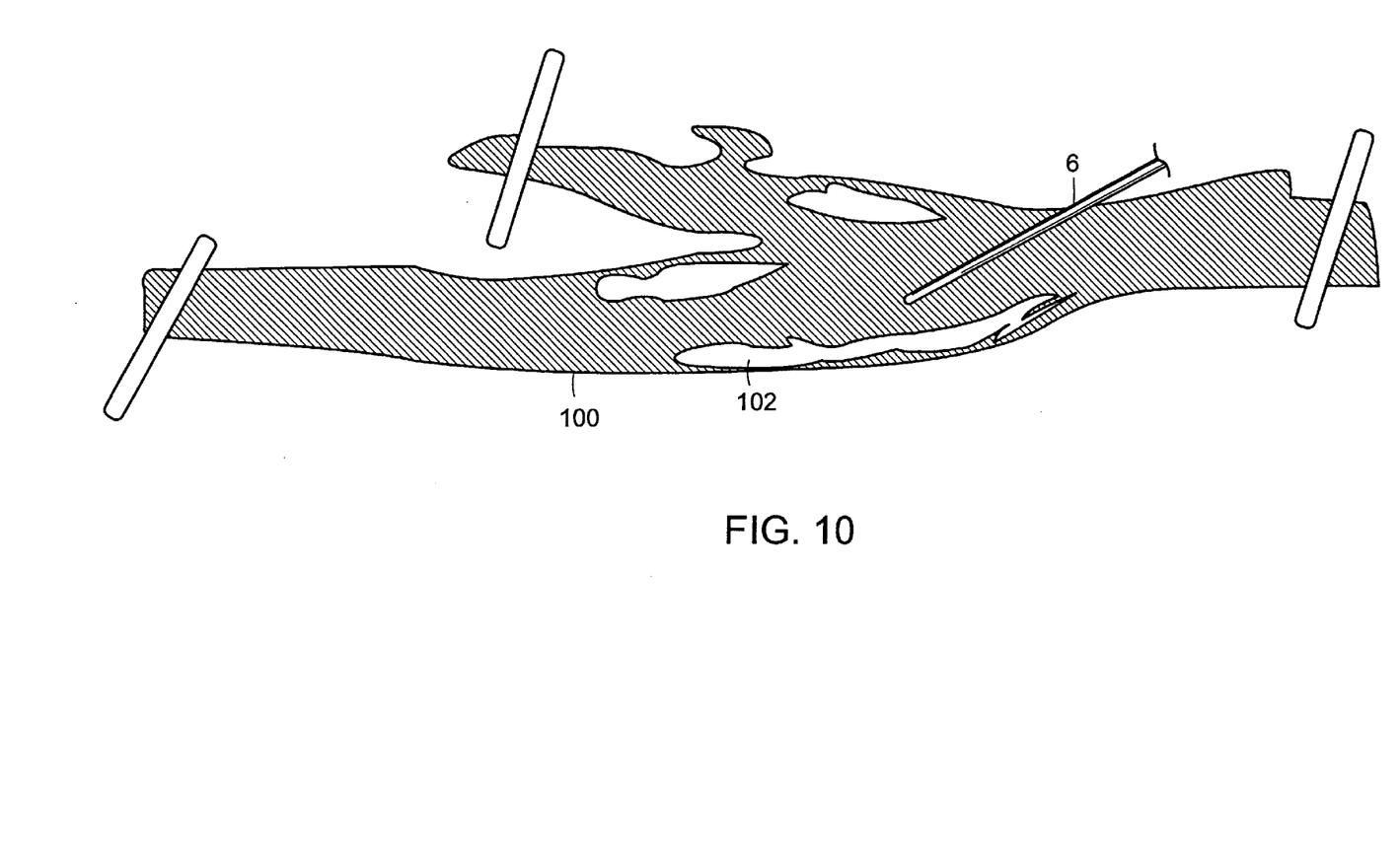
FIG. 10 is a cross-sectional view of a patient's carotid artery during a debulking operation using one embodiment of the present invention.
Figure 11:
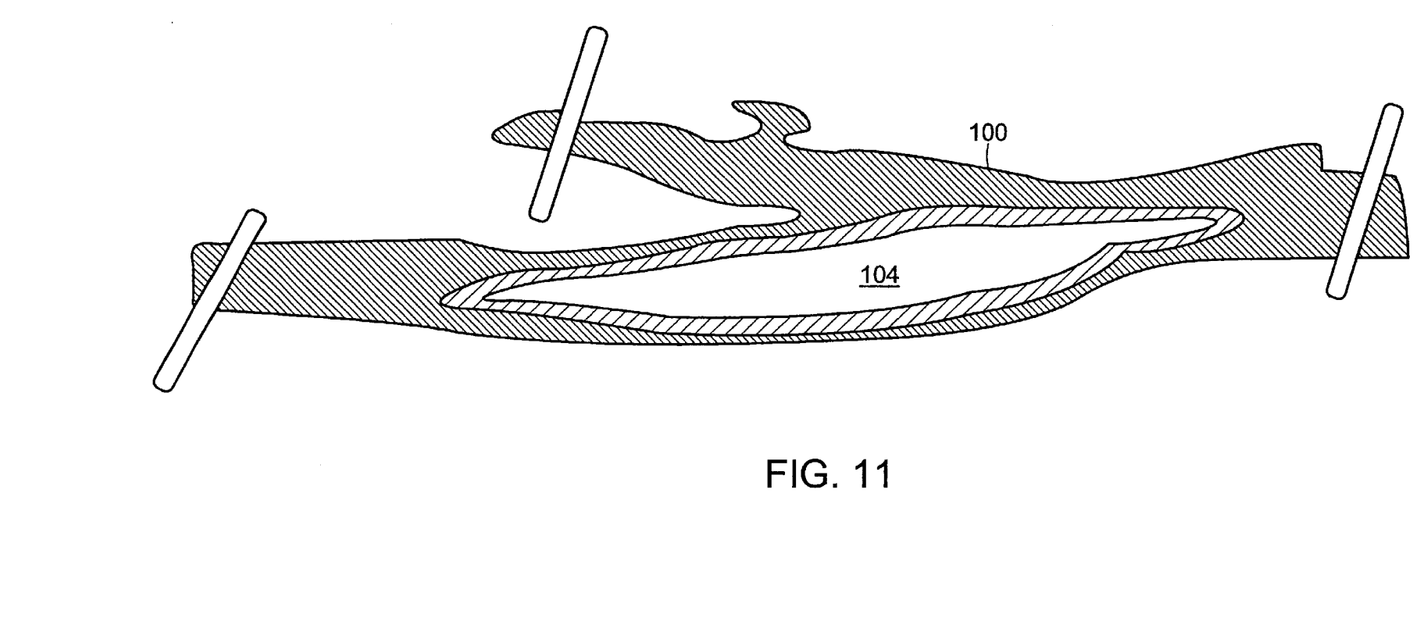
FIG. 11 is a cross-sectional view of a patient's carotid artery during a debulking operation as shown in FIG. 10 after plaque has been ablated.

FIGS. 10 and 11 show the manner in which the embodiment shown in FIGS. 6 and 8 may be used to debulk the carotid artery.

In a preferred embodiment of the invention, maximum vibratory motion is not confined to the tip of the probe as in the case of prior art ultrasonic instruments. Rather, the probe of the invention is specially designed to provide a multiplicity of so-called anti-nodes (i.e., points along the probe where maximum vibration occur) at spaced intervals along the axial length of the probe, in addition to the tip of the probe. This construction best suits the method of the invention because removal of plaque 102 in artery 100 will not be confined to those regions coming into contact with the tip of the probe. Rather, as the probe is inserted through artery 100, plaque 102 is removed in all areas adjacent to the multiplicity of anti-nodes located along the entire length of the probe. In this way, the apparatus of the invention allows for removal of plaque 102 in accordance with the method of the invention to be carried out most efficiently so that actual treatment time is greatly reduced as compared to prior art methods.

As shown in FIG. 11, the energy reduces plaque 102 (shown in FIG. 10) to a particulate material 104 and simultaneously the probe moves towards areas of greater mass within the lumen. The term "plaque" is used herein to denote not only fatty deposits but any other type of build-up that can cause or contribute to stenosis or occlusion within a blood vessel, such as calcium deposits. This is due to negative pressure gradients around and near the probe. The probe can make contact with the inner surface of the vessel without causing damage to the tissue. The probe is a non-fibro intimal hyuperplasia causing device.

The mode of vibration of the ultrasound probe in the apparatus of the invention differs from the axial mode of vibration which is conventional in the prior art. Rather than vibrating exclusively in the axial direction, the probe in the apparatus of the present invention vibrates in a direction transverse to the axial direction. Because of this transverse mode of vibration, the probe of the invention removes plaque not just at those points where the probe makes actual contact with the tissue, but also typically in a region having a radius up to 1.0–1.5 mm around the probe. Hence, the transverse mode of vibration of the probe used in the present apparatus also contributes to the efficiency of the method of the invention by expanding the coverage area around the probe where tissue is removed.

In general, in order to increase the number of anti-nodes occurring along the axial length of the probe, the vibration frequency imparted to the probe should be increased. The frequency, however, is not critical and a generator run at 20 kHz is generally sufficient to provide for an effective number of anti-nodes along the axial length of the probe. In addition, as will be appreciated by those skilled in the art, it is possible to adjust the dimensions of the probe, including diameter, length and location of coupling to the ultrasonic energy source, in order to space the anti-nodes at desired intervals.

An ultrasonic medical apparatus which operates in the transverse mode and which is suitable for carrying out the method of the present invention is disclosed in application Ser. No. 09/618,352, the disclosure of which is incorporated herein by reference.

Thus, there is shown and described a unique design and concept of an ultrasonic treatment device and method of its use. While this description is directed to particular embodiments, it is understood that those skilled in the art may conceive modifications and/or variations to the specific embodiments shown and described herein. Any such modifications or variations which fall within the purview of this description are intended to be included as part of the invention. It is understood that the description herein is intended to be illustrative only and is not intended to be limitative. Rather, the scope of the invention described herein is limited only by the claims.

What is claimed is:

1. An ultrasonic apparatus for removing plaque from a blood vessel comprising:
    an elongate probe having proximal and distal extremities, the elongate probe being sized so that it can be introduced into a blood vessel and having a length so that when the distal extremity is disposed in the vicinity of a plaque on the inner surface of the vessel the proximal extremity is outside of a body of a treated patient, the elongate probe having a passage extending from the proximal extremity to the distal extremity;
    a probe tip disposed in the passage, the probe tip being capable of conducting ultrasonic energy into the plaque on the vessel for cavitating the plaque;
    an ultrasonic generator which is capable of delivering ultrasonic energy to the probe and into the plaque to debulk the vessel by reduction of the plaque to a particulate material;
    a handle coupled to the proximal extremity of the elongate probe, wherein a plurality of transverse anti-nodes along at least a portion of the length of the elongate probe create a plaque destroying effect along at least a portion of the length of the elongate probe.

2. The apparatus according to claim 1 further comprising:
    fenestrations disposed along the length of the probe for use in at least one of irrigation and aspiration.

3. The apparatus according to claim 1 wherein:
    the ultrasonic generator is configured to run at about 20 kHz.

4. The device of claim 1 wherein the elongate probe comprises an at least one channel for aspiration of the particulate material from a treatment site.

5. The device of claim 1 wherein the ultrasonic generator generates a transverse ultrasonic vibration along a portion of the length of the elongate probe.

6. The device of claim 1 wherein a transverse ultrasonic vibration is transmitted from the ultrasonic generator to the elongate probe through an ultrasonic coupler.

7. The device of claim 1 wherein the ultrasonic generator engages the proximal extremity of the elongate probe through an ultrasonic coupler.

8. The device of claim 1 wherein the elongate probe is axially movably mounted within an aspiration sheath.

9. The device of claim 1 wherein the elongate probe vibrates in a direction transverse to at least a portion of the length of the elongate probe.

10. The device of claim 1 wherein a transverse ultrasonic vibration of the elongate probe provides a plurality of transverse anti-nodes along at least a portion of the length of the elongate probe.

11. The device of claim 1 wherein a transverse ultrasonic vibration of the elongate probe creates a plaque destroying effect along at least a portion of the length of the elongate probe.

12. The device of claim 1 wherein the elongate probe reduces the plaque to the particulate material having a diameter of approximately 10 microns or less.

13. An ultrasonic medical device for destroying a plaque within a blood vessel comprising:
    a probe having a distal end, a proximal end and an axial length therebetween;
    a diameter of the probe that is tapered from the proximal end of the probe to the distal end of the probe; and
    an ultrasonic generator that engages the proximal end of the probe to deliver an ultrasonic energy to the probe, wherein the probe supports a transverse ultrasonic vibration creating a plurality of transverse anti-nodes causing a plaque destroying effect along at least a portion of the axial length of the probe to destroy the plaque within the blood vessel.

14. The device of claim 13 wherein the ultrasonic generator produces the transverse ultrasonic vibration along a portion of the axial length of the probe.

15. The device of claim 13 wherein the transverse ultrasonic vibration of the probe creates a plaque destroying effect along at least a portion of the axial length of the probe.

16. The device of claim 13 wherein a transmission of the ultrasonic energy to the probe is at a power level to reduce the plaque to a particulate material having a diameter of approximately 10 microns or less.

17. The device of claim 13 wherein the transverse ultrasonic vibration is transmitted from the ultrasonic generator to the probe through an ultrasonic coupler.

18. The device of claim 13 wherein the ultrasonic generator engages the proximal end of the probe through an ultrasonic coupler.

19. The device of claim 13 wherein the probe has a small cross sectional profile.

20. The device of claim 13 wherein the probe is axially movably mounted within an aspiration sheath.

21. The device of claim 13 further comprising a probe tip capable of moving axially inward and outward relative to a distal end of an aspiration sheath.

22. The device of claim 13 wherein the probe comprises a channel for aspiration of a particulate material from the blood vessel.

23. The device of claim 13 wherein the probe vibrates in a direction transverse to at least a portion of the axial length of the probe.

24. The device of claim 13 wherein the transverse ultrasonic vibration of the probe provides a plurality of transverse anti-nodes along at least a portion of the axial length of the probe.

25. The device of claim 24 wherein the transverse anti-nodes are points of a maximum transverse ultrasonic vibration along at least a portion of the axial length of the probe.

26. The device of claim 13 wherein a flexibility of the probe allows the probe to be articulated within the blood vessel.

27. An ultrasonic medical device for ablating a plaque within a blood vessel comprising:
a flexible probe having a distal end, a proximal end and an axial length therebetween;
a probe tip extending from the distal end of the flexible probe; and an ultrasonic generator that engages the proximal end of the flexible probe to deliver an ultrasonic energy along the axial length of the flexible probe,
wherein the flexible probe is capable of flexing to support a transverse ultrasonic vibration creating a plurality of transverse anti-nodes causing a plaque destroying effect along at least a portion of the axial length of the flexible probe.

28. The device of claim 27 wherein the ultrasonic generator produces the transverse ultrasonic vibration along a portion of the axial length of the flexible probe.

29. The device of claim 27 wherein the transverse ultrasonic vibration of the flexible probe creates a plaque ablating effect along at least a portion of the axial length of the flexible probe.

30. The device of claim 27 wherein a transmission of the ultrasonic energy to the flexible probe is at a power level to reduce the plaque to a particulate material having a diameter of approximately 10 microns or less.

31. The device of claim 27 wherein the transverse ultrasonic vibration is transmitted from the ultrasonic generator to the flexible probe through an ultrasonic coupler.

32. The device of claim 27 wherein the ultrasonic generator engages the proximal end of the flexible probe through an ultrasonic coupler.

33. The device of claim 27 wherein the flexible probe has a small cross sectional profile.

34. The device of claim 27 wherein the flexible probe is axially movably mounted within an aspiration sheath.

35. The device of claim 27 wherein the probe tip is capable of moving axially inward and outward relative to a distal end of an aspiration sheath.

36. The device of claim 27 wherein the flexible probe comprises a channel for aspiration of a particulate material from the blood vessel.

37. The device of claim 27 wherein the flexible probe vibrates in a direction transverse to at least a portion of the axial length of the flexible probe.

38. The device of claim 27 wherein the transverse ultrasonic vibration of the flexible probe provides a plurality of transverse anti-nodes along at least a portion of the axial length of the flexible probe.

39. The device of claim 38 wherein the transverse anti-nodes are points of a maximum transverse ultrasonic vibration along at least a portion of the axial length of the flexible probe.

40. The device of claim 27 wherein a flexibility of the flexible probe allows the flexible probe to be articulated within the blood vessel.

* * * * *